United States Patent

Banet et al.

[11] Patent Number: 6,069,703
[45] Date of Patent: May 30, 2000

[54] METHOD AND DEVICE FOR SIMULTANEOUSLY MEASURING THE THICKNESS OF MULTIPLE THIN METAL FILMS IN A MULTILAYER STRUCTURE

[75] Inventors: Matthew J. Banet, Boston; Martin Fuchs, Uxbridge, both of Mass.; John A. Rogers, Castle Rock, Colo.; Keith A. Nelson, Newton, Mass.; Timothy F. Crimmins; Alexei Maznev, both of Cambridge, Mass.

[73] Assignee: Active Impulse Systems, Inc., Natick, Mass.

[21] Appl. No.: 09/086,975

[22] Filed: May 28, 1998

[51] Int. Cl.[7] ............................ G01N 21/00; G01N 29/04
[52] U.S. Cl. .............................. 356/432; 356/381; 73/801
[58] Field of Search ........................ 356/381, 432, 356/432 T, 357; 73/801, 800

[56] References Cited

U.S. PATENT DOCUMENTS

| | | |
|---|---|---|
| 3,462,223 | 8/1969 | Tiemann et al. . |
| 4,522,510 | 6/1985 | Rosencwaig et al. . |
| 4,655,547 | 4/1987 | Heritage et al. . |
| 4,710,030 | 12/1987 | Tauc et al. . |
| 4,728,165 | 3/1988 | Powell . |
| 4,812,036 | 3/1989 | Inoue . |
| 4,939,368 | 7/1990 | Brown . |
| 5,062,693 | 11/1991 | Beratan et al. . |
| 5,132,824 | 7/1992 | Patel et al. . |
| 5,220,403 | 6/1993 | Batchelder et al. . |
| 5,263,039 | 11/1993 | Skupsky et al. . |
| 5,285,438 | 2/1994 | Marchand et al. . |
| 5,344,236 | 9/1994 | Fishman . |
| 5,361,638 | 11/1994 | Pettersson et al. . |
| 5,438,879 | 8/1995 | Reda . |
| 5,479,256 | 12/1995 | Tamai et al. . |
| 5,546,811 | 8/1996 | Rogers et al. . |
| 5,633,711 | 5/1997 | Nelson et al. . |
| 5,672,830 | 9/1997 | Rogers et al. . |
| 5,734,470 | 3/1998 | Rogers et al. . |
| 5,748,318 | 5/1998 | Maris et al. .................... 356/381 |

FOREIGN PATENT DOCUMENTS

WO9803044 A1  1/1998  WIPO .

OTHER PUBLICATIONS

International Search Report.
Allen et al., "Microfabricated Structures for the in situ Measurement of Residual Stress, Young's Modulus, and Ultimate Strain of Thin Films", Appl. Phys. Lett., 51:241–243, 1987.

(List continued on next page.)

Primary Examiner—Frank G. Font
Assistant Examiner—Zandra Smith
Attorney, Agent, or Firm—Tony E. Piotrowski

[57] ABSTRACT

An apparatus for measuring a property of a structure comprising at least one layer, the appratus including a light source that produces an optical pulse having a duration of less than 10 ps; a diffractive element that receives the optical pulse and diffracts it to generate at least two excitation pulses; an optical system that spatially and temporally overlaps at least two excitation pulses on or in the structure to form an excitation pattern, containing at least two light regions, that launches an acoustic wave having an out-of-plane component that propagates through the layer, reflects off a lower boundary of the layer, and returns to a surface of the structure to modulate a property of the structure; a light source that produces a probe pulse that diffracts off the modulated property to generate at least one signal pulse; a detector that receives at least one signal pulse and in response generates a light-induced electrical signal; and an analyzer that analyzes the light-induced electrical signal to measure the property of the structure.

38 Claims, 6 Drawing Sheets

OTHER PUBLICATIONS

Bauer et al., "Determination of the Stresses and Properties of Polymer Coatings", J. of Coatings Technology, 60:51–55, 1988.

Coburn et al., "Stress in Polyimide Coatings", J. of Polymer Science: Part B: Polymer Physics, 32:1271–1283, 1994.

Duggal et al., "Resolution of Conflicting Descriptions of Propylene Glycol Relaxation Dynamics Through Impulsive Stimulated Scattering Experiments", Polymer Communications, 32:356–360, 1991.

Duggal et al., "Real–Time Optical Characterization of Surface Acoustic Modes of Polymide Thin–Film Coatings", J. Appl. Phys. 72:2823–2839, 1992.

Fishman et al., "Surface Selectivity in Holographic Transient Grating–Diffraction", Stanford University, Stanford, CA; W.W. Hansen Exp. Phys. Lab. & Dept. of Chemistry.

Goldsmith et al., "Measurement of Stresses Generated to Cured Polyimide Films", J. Vac. Sci. Technol. 1:407–409, 1983.

Head et al., "Determination of Shear Stress at a Solder Paste/Stencil Interface", Mat. Res. Soc. Symp. Proc. 323:425–433, 1994.

Maden et al., "Stress Analysis of Thin Polyimide Films Using Holographic Interferometry", Experimental Mechanics 31:179–184, 1991.

Rogers et al., "Study of Lamb Acoustic Waveguide Modes in Unsupported Polyimide Thin Films Using Real–Time Impulsive Stimulated Thermal Scattering", J. Appl. Phys. 75:1534–1556, 1994.

Rogers et al., "Real–Time In Situ Characterization of Thin Films", CHEMF. 8, 27 (1992), pp. 4–8.

Duggal, "Picosecond–Microsecond Structural Relaxation Dynamics in Polypropelyne Glycol", Journal of Chemical Physics, No. 94, pp. 7677–7688, Jun. 15, 1991.

Whitman et al., Appl. Optics, 8, 1567 (1969).

Nizzoli et al., Dynamical Properties of Solids (ed. G.K. Horton et al., North–Holland Amsterdam, 1990) vol. 6, 283.

Bortolani et al., J. Phys. C., 16, 1757 (1983).

Fishman I.M. et al., "Surface Selectivity in Four–Wave Mixing: Transient Gratings as a Theoretical and Experimental Example", J. Opt. Soc. Am. B., vol. 8, No. 9, Sep. 1991, pp. 1880–1888.

Barish et al., "Photoinduced Ionization of Bovine Serum Albumin by Holographic Relaxation Methods", J. Chem. Phys. 85:4194–4195, 1986.

Burzynski et al., "Study of Anisotrophy of Acoustic Wave Propagation in Stretched poly(vinylidene difluoride) Film Using the Picosecond Transient Grating Technique", Polymer, 30:1247–1250, 1989.

Deeg et al., "New Grating Experiments in the Study of Irreversible Photochemical Reactions", IEEE J. Quantum Electronics, QE–22:1476–1481, 1986.

Espinet et al., "Laser–induced Gratings in Nematic/Cholesteric Mixtures", App. Phys. Letters, 50:1924–1926, 1987.

Meth et al., "Experimental and Theoretical Analysis of Transient Grating Generation and Detection of Acoustic Waveguide Modes in Ultrathin Solids", J. App. Phys. 67:3362–3377, 1990.

Greene et al., Picosecond Relaxation Dynamics in Polydiacetylene–pTs, Chem. Phys. Letters, 139:381–385, 1987.

Meth et al., "Generation and Detection of Acoustic Waveguide Modes in Ultrathin Crystals Using the Transient Grating Technique", Chem. Phys. Letters, 162:306–312, 1989.

Nelson et al., "Optical Generation of Tunable Ultrasonic Waves", J. App. Phys., 53:1144–1149, 1982.

Nizzoli, "Problems with the Determination of Elastic Constants from Higher–Order Surface Waves: Results for Al on NaCl", Physical Review B, 37:1007–1010, 1988.

Noll et al., "Picosecond Photoinduced Index Changes in a Si:H and Related Alloys Measured by Transient Grating Experiments", J. Non–Crystalline Solids, 97 & 98:141–144, 1987.

Portella et al., "Four–Wave Mixing Experiments in Cresyl Violet Thin Films: Inadequacy of a Two–Level Interpretation", J. Phys. Chem., 91:3715–3719, 1987.

Prasad, "Non–Linear Optical Effects in Thin Organic Polymeric Films", Thin Solid Films, 152:275–294, 1987.

Rao et al., "Third Order Nonlinear Optical Interactions in Thin Films by Poly–p–phenylenebenzobisthiazole Polymer Investigated by Picosecond and Subpicosend Degenerate Four Wave Mixing", App. Phys. Letters, 48:1187–1189, 1986.

Rao et al., "Picosecond Transient Grating Studies of Polymeric Thin Films", App. Phys. Letters, 48:387–389, 1986.

Rose et al., Picosecond Transient Grating Transport in Anthracene Single Crystals, Measurements of Singlet Excitation, Chem. Phys. Letters, 106:13–19, 1984.

Rao et al., "Picosecond Laser–Induced Transient Grating Probe of the Mechanical Properties of High–Modulus Poly(p–phenylenebenzobisoxazole–2.6–diyl)", Macromolecules, 22:985–989, 1989.

Rothenhausler, "Plasmon Surface Polariton Fields for the Characterization of Thin Films", Thin Solid Films, 159:323–330, 1988.

A.R. Duggal et al., "Real–time Characterization of Acoustic Modes of Polyimide Thin–Film Coatings Using Impulsive Stimulated Thermal Scattering", App. Phys. Lett., 60(6) Feb. 10, 1992, pp. 692–694.

METHOD AND DEVICE FOR SIMULTANEOUSLY MEASURING THE THICKNESS OF MULTIPLE THIN METAL FILMS IN A MULTILAYER STRUCTURE

BACKGROUND OF THE INVENTION

This invention relates to a method and apparatus for simultaneously determining the thickness of multiple thin films (e.g., metal films) contained in a multilayer structure (e.g., a microelectronic device).

During fabrication of microelectronic devices, thin films of metals and metal alloys are deposited on silicon wafers and used as electrical conductors, adhesion-promoting layers, and diffusion barriers. Microprocessors, for example, use metal films of copper, tungsten, and aluminum as electrical conductors and interconnects; titanium and tantalum as adhesion-promoting layers; and titanium:nitride and tantalum:nitride as diffusion barriers. Thickness variations in these films can modify their electrical and mechanical properties, thereby affecting the performance of the microprocessor. The target thickness values of metal films vary depending on their function: conductors and interconnects are typically 3000–10000 angstroms thick, while adhesion-promoting and diffusion-barrier layers are typically between 100–500 angstroms thick.

Metal films are typically deposited and patterned in complex geometries in the microprocessor. A geometry currently used in microelectronics fabrication is a "damascene" or "dual damascene" structure. Damascene-type structures, used primarily to form copper conductors and interconnects, are typically formed by a multi-step process: i) an oxide layer on a wafer is first etched to have a series of trenches and then coated with a diffusion-barrier layer of tantalum or tantalum nitride; ii) copper is electrolytically plated onto the wafer to fill the coated trenches; iii) the structure is then mechanically polished to remove excess copper, leaving only trenches filled with the diffusion-barrier layer and copper. The resulting structure is a series of separated copper lines having a thickness of a few thousand angstroms, a width and periodicity of about 0.5 microns, and a length of several millimeters.

During typical fabrication processes, films are deposited to have a thickness of within a few percent (e.g., 5–100 angstroms, a value roughly equivalent to one or two seconds of human fingernail growth) of their target value. Because of these rigid tolerances, film thickness is often measured as a quality-control parameter during and/or after the microprocessor's fabrication. Noncontact, nondestructive measurement techniques (e.g., optical techniques) are preferred because they can measured patterned "product" samples, (e.g., damascene samples) rather than "monitor" samples. Measurement of product samples accurately indicates errors in fabrication processes and additionally reduces costs associated with monitor samples.

One optical technique for film-thickness measurements uses a single, short (typically $100 \times 10^{-15}$ seconds, i.e. 100 fs) optical pulse to generate an acoustic pulse that propagates into a multilayer structure. The acoustic pulse reflects off various interfaces (i.e., layer/layer and substrate/layer interfaces) in the structure, thus causing it to return to the structure's surface. The returning pulse modulates the surface reflectivity and is measured with a variably delayed optical probe pulse. The thickness of the layers in the structure is determined by analyzing the time dependence of the reflected probe beam and the sound velocities of the acoustic pulse.

A related method splits a single short optical pulse into two spatially separate pulses using a partially reflecting mirror (e.g., a beam-splitter). A lens collects and overlaps the two optical pulses on a structure's surface to form an interference pattern containing periodic "light" (constructive interference) and "dark" (destructive interference) regions. The sample absorbs light in each of the light regions to generate an acoustic wave that includes a component that propagates into the structure and reflects off the various interfaces. A probe beam diffracts off the reflected acoustic waves that return to the surface to form a signal beam that is analyzed as described above.

SUMMARY OF THE INVENTION

In general, in one aspect, the invention provides both a method and apparatus for measuring the thickness of one or more layers in a structure. The apparatus features a light source that produces an optical pulse having a duration of less than 10 ps, and a diffractive mask that receives the optical pulse and diffracts it to generate at least two excitation pulses. Once the excitation pulses are generated, an optical system collects and overlaps them on or in the structure to form an excitation pattern containing at least two light regions. The pattern launches an acoustic wave out of the plane of the layers. A portion of the wave propagates through the first layer, reflects off its lower boundary, and returns to a surface of the structure to modulate either: i) its optical reflectivity; or ii) its surface to generate a time-dependent "ripple". Both of these processes are spatially periodic. The acoustic wave is also reflected at the interfaces separating each layer in the structure. A variably delayed probe pulse then diffracts off the surface to generate at least one signal pulse that is spatially separate from the reflected probe pulse. A detector receives the signal pulse, and in response generates a light-induced electrical signal that is processed with an analyzer to measure the thickness of one or more of the layers in the structure.

A diffractive mask can be any optical element that diffracts an incident optical beam into two or more optical beams. In one embodiment, the diffractive mask features an optically transparent substrate that includes a series of diffractive patterns. Each pattern contains a series of parallel trenches having a depth (d) that is related to the wavelength ($\lambda$) and reflective index (n) of the phase mask: $d=\lambda/2n$. Each pattern typically has a spatial periodicity of between 0.1 and 100 microns. The patterns are designed such that the diffracted excitation pulses leaving the mask include phase fronts that are approximately parallel when overlapped by the optical system. In this way, the phase fronts of the overlapped optical pulses interfere to form a series of alternating light and dark regions that extend along an entire area of the overlapped optical pulses. As is described in detail below, this increases the magnitude of the diffracted signal, thereby enhancing the sensitivity of the measurement.

In other embodiments, the optical system is an imaging system that includes at least one lens (contained, e.g., in an achromat lens pair) that collects and overlaps the excitation pulses on or in the structure with a magnification ratio of about 1:1. In this configuration, the lens can be positioned to additionally receive: i) the probe pulse and focus it onto the excitation pattern; and ii) at least one signal beam and focus it onto the detector. In other embodimets the optical system includes a pair of mirrors that direct the excitation beams onto the sample.

The light source is typically a laser that generates an optical pulse having a duration of 2 ps or less and a wavelength that is at least partially absorbed by the sample. For example, the laser can be a titanium:sapphire, chromium:LISAF, ring, or fiber laser. The apparatus typically includes a mechanical delay line that delays the probe pulse relative to the excitation optical pulses. The mechanical delay line can, for example, include a galvanometer, rotating mirror, piezoelectric device, an optical fiber, or equivalent means to delay the probe pulse. In still other embodiments, the apparatus further includes an optical heterodyne pulse configured to overlap with one of the signal beams on a light-sensitive region of the detector. This amplifies the detected signal to additionally enhance the measurement.

In another aspect, the apparatus described above is configured to excite and detect both in-plane and out-of-plane acoustic waves in a sample (e.g., a multilayer structure). In this case, the apparatus is similar to that describe above, but additionally includes a second probe beam from a second light source to measure acoustic waves propagating in the plane of the structure. The second probe beam is aligned to diffract off a modulation on the surface of the sample (e.g., a modulated surface reflectivity or surface ripple) caused by the in-plane acoustic wave to generate a second signal pulse. This signal pulse is measured with a second detector. An analyzer (e.g., an appropriately programmed computer) then processes the first light-induced electrical signal (from the out-of-plane acoustic pulses) and the second light-induced electrical signal (from the in-plane acoustic pulses) to measure a property of structure. For example, the computer can compare the light-induced electrical signal to a mathematical function that models, e.g., strain induced in the structure by the excitation pattern.

In this embodiment, the second light source is typically a diode laser that generates a continuous wave beam or a pulsed beam (typically having a duration of greater than 100 ns). The analyzer is configured to analyze the second light-induced electrical signal to determine one or more of the following properties: i) the thickness of the structure; ii) the thickness of a layer in the structure; iii) a density of a layer in the structure; and iv) a mechanical or elastic property of a layer in the structure. For example, the structure measured with this apparatus can contain multiple layers, and the analyzer can be configured to analyze the first and second light-induced electrical signals to determine the thickness of each layer in the structure.

Both the method and apparatus described above have many advantages. In particular, the apparatus simultaneously and effectively measures the thickness of each layer in a multilayer structure. These values can then be used to control a fabrication process (e.g., fabrication of a microelectronic device). The invention features all the advantages of optical metrology: measurements are noncontact, rapid and remote, and can be made over a small region. Data are collected in less than a few seconds from a single measurement point typically having an area of between 10 and 100 microns in less than a few seconds. From these data film thickness is determined with an accuracy and repeatability of a few angstroms.

Use of diffractive optics (e.g., a phase mask) in the optical system has particular advantages, especially when used to separate a single optical pulse having a duration of less than about 1 ps. For example, the number of spatially periodic "light" regions in an excitation pattern decreases with the duration of the optical pulses forming the pattern. For pulses less than 1 ps, this can severely decrease the number of ripples on the sample's surface generated by the pattern, thereby decreasing the magnitude of the diffracted signal beam. This makes it difficult or impossible to detect relatively weak (but very important) features in the signal beam.

In general, pulses separated by a phase mask produce significantly stronger signal beams compared to those generated by pulses separated by conventional beam-splitting methods relying on partially reflecting mirrors. This is because the pulses leaving the phase mask have parallel "phase fronts", while pulses separted by a partially reflecting mirror have angled phase fronts. When overlapped in a sample, the parallel phase fronts optically interfere over the entire area of the incident optical beams, and thus produce many more light regions than the angled phase fronts. As described above, this increases the amount of ripple on the surface or the area of modulated surface reflectivity, thereby increasing the diffraction efficiency of the probe pulse at the sample's surface. This increases the magnitude of the signal beam and consequently the likelihood that weak features in the signal beam are detected. Another advantage is that when used with short optical pulses, a properly designed phase mask generates patterns of light regions (e.g., having multiple spatial frequencies) that can measure damascene-type or related structures having complex cross-sectional geometries (e.g., a stepped cross section).

An additional advantage of the apparatus is that a spatially periodic excitation pattern launches both in-plane and out-of-plane acoustic waves, both of which can be simultaneously detected and analyzed to determine properties of the film. Analysis of in-plane acoustic waves is described, for example, in U.S. Pat. No. 5,633,711 (entitled MEASUREMENT OF MATERIAL PROPERTIES WITH OPTICALLY INDUCED PHONONS), U.S. Pat. No. 5,546,811 (entitled OPTICAL MEASUREMENT OF STRESS IN THIN FILM SAMPLES), and U.S. Ser. No. 08/783,046 (entitled METHOD AND DEVICE FOR MEASURING FILM THICKNESS), the contents of which are incorporated by reference.

Use of a spatially periodic excitation pattern to measure acoustic waves propagating into a film has still other advantages. In this geometry, for example, the signal beam is diffracted, and is thus spatially separated from the reflected probe beam. Since typical signal beams have magnitudes that are $1e^{-4}-1e^{-6}$ times smaller than those of the reflected beam, spatial separation makes signal detection significantly easier, thereby increasing the quality of the data.

Other features, aspects, and advantages of the invention follow from the following detailed description, and from the claims.

DETAILED DESCRIPTION

Figure 1:
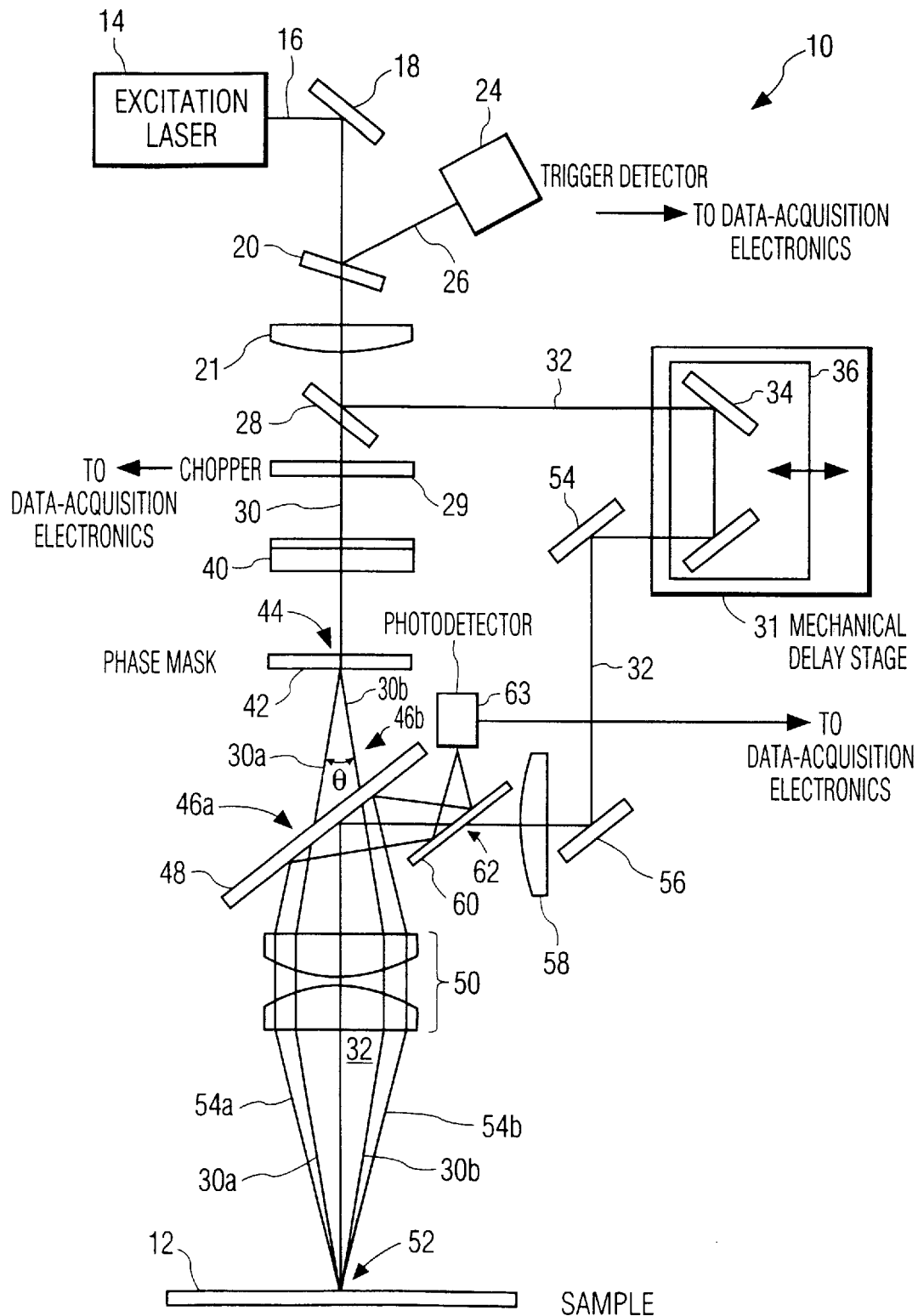
FIG. 1 is a schematic side view of an optical system for exciting and measuring out-of-plane acoustic waves in a multilayer structure.

FIG. 1 shows an optical system 10 that initiates and measures both in-plane and out-of-plane acoustic waves to simultaneously determine the thickness of each layer in a multilayer structure 12. The system 10 features an excitation laser 14 that generates a single excitation beam 16 containing an excitation pulse having a duration of about 100 fs, a wavelength of about 800 nm, and an energy of about 10 µJ/pulse. The excitation laser is typically a mode-locked ti:sapphire laser, fiber laser, or another light source generating a similar optical pulse.

The excitation beam 16 reflects off a mirror 18 and propagates through a glass plate 20 that reflects a portion 26 of the beam 16 into a trigger detector 24. After receiving a portion of the beam, the trigger detector generates an electrical signal that is sent to a series of data-acquisition electronics for analysis. The transmitted beam passes through a collimating lens 21 and impinges a partially reflecting mirror 28 that transmits a beam 30 having an intensity that is about 90% of the incident beam. This portion of the beam eventually forms an excitation pattern 52 that stimulates acoustic pulses in the sample 12. So that the eventual signal beam can be monitored using phase-sensitive detecting electronics (e.g., a lock-in amplifier), the beam 30 passes through a chopper 29 (e.g., an acousto-optic modulator, such as a Bragg cell) that modulates it at a high frequency (typically 1 MHz or higher). An electrical signal at this frequency is sent to the data-acquisition electronics to serve as a trigger. Following modulation, a cylindrical lens 40 focuses the chopped beam 30 onto a phase mask 42 that includes a series of patterns 44. Each pattern 44 is etched to contain a series of periodic trenches having depth (d) chosen to maximize diffraction of the incident optical wavelength and a period selected for the material being measured (d~$\lambda$/2n). The pattern diffracts the single excitation beam into a pair of beams 30a, 30b separated by an angle $\theta$. Such a phase mask is described in U.S. Pat. No. 5,734,470, entitled DEVICE AND METHOD FOR TIME-RESOLVED OPTICAL MEASUREMENTS, the contents of which are incorporated by reference.

The beams 30a, 30b pass through a pair of slots 46a, 46b drilled into a high-reflecting mirror 48 coated to reflect the wavelength of the incident optical beam. An achromat lens pair 50 receives the transmitted beams 30a, 30b and overlaps them on the sample 12 to form the optical excitation pattern 52. The optical excitation pattern 52 initiates acoustic waves that propagate into the sample as described in more detail below.

A portion 32 of the beam 30 is reflected by the partially reflecting mirror 28 into a mechanical delay stage 31 and is used to probe the acoustic waves in the sample. The stage 31 includes a pair of mirrors 34 and a movable, electronically controlled device 36 that scans back and forth in response to an electrical signal. The scanning process delays a probe pulse contained in the probe beam 32 relative to the excitation pulse, allowing the time dependence of the acoustic pulses to be monitored with high-temporal resolution (e.g., less than 1 ps). The scanning device, for example, can be a galvonometer or a piezoelectric stage. Once delayed, the probe beam 32 reflects off a first 54 and second 56 mirror, and is collimated by a lens 58. The beam then passes through a hole 62 drilled in a mirror 60 coated to have a high reflectivity at the wavelength of the probe beam. The beam 32 reflects off the high-reflecting mirror, propagates through the same achromat lens pair 50 used to focus the excitation beams, and irradiates a spot on the sample 12 previously irradiated by the excitation pattern 52.

As described in more detail below, a portion of the probe beam is diffracted by the acoustic waves to form a pair of signal beams 54a, 54b that propagate away from the sample 12. The signal beams 54a, 54b are generated at the frequency used to modulate the excitation beam 30. Those beams then pass through the achromat pair lens 50, and irradiate the high-reflecting mirror 48 near the outside edges of the drilled holes 46a, 46b. The mirror 48 reflects the signal beams on each side of the hole 62 drilled in the mirror 60. The mirror 60 reflects the signal beams into a photodetector 63 that generates an electrical signal in response to the incident radiation. The electrical signal is then sent to the data-acquisition electronics, where it is analyzed by the phase-sensitive lock-in amplifier at the modulation frequency.

Figure 2A:
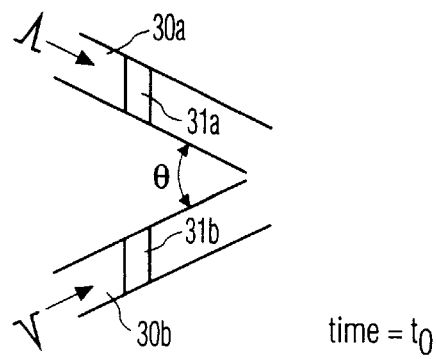
FIGS. 2A and 2B are, respectively, schematic drawings of two optical pulses separated with a phase mask prior to and during overlap according to the method of the invention.
Figure 2B:
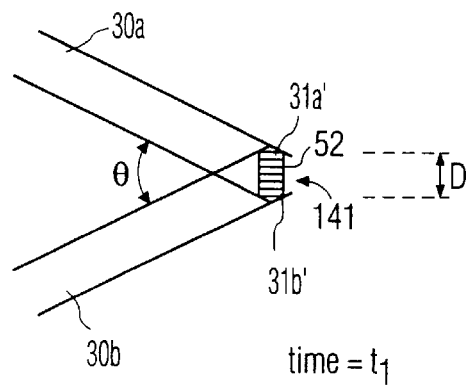
Figure 3A:
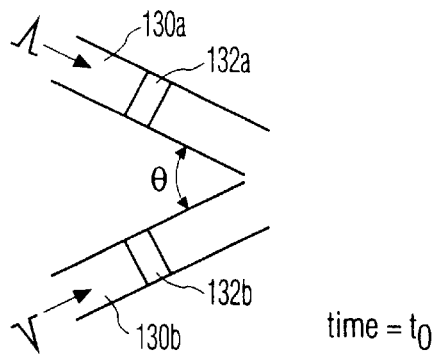
FIGS. 3A and 3B are, respectively, schematic drawings of two optical pulses separated with a partially reflecting mirror prior to and during overlap according to the prior art.
Figure 3B:
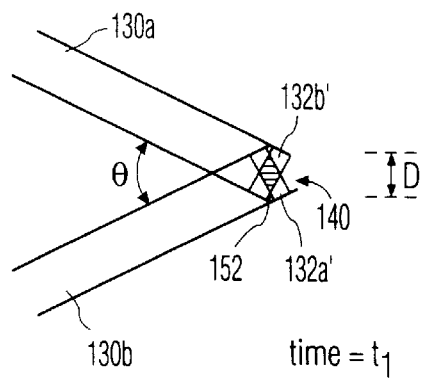

Use of a phase mask in the above-described optical system generates alternating light regions over the entire area of the excitation pattern, thereby increasing the signal-to-noise ratio of the signal waveform and improving the accuracy and precision of the thickness measurement. FIGS. 2a, b and 3a, b illustrate this point, showing excitation patterns (52 in FIG. 2B; 152 in FIG. 3B) formed by crossing a pair of short pulses separated by a phase mask (FIGS. 2a, 2b) and a partially reflecting mirror (FIGS. 3a, 3b) of the prior art. FIGS. 3a and 3b show that at time=$t_0$ optical pulses 130a, 130b separated by a partially reflecting mirror contain phase fronts 132a, 132b. When these pulses converge at an angle $\theta$ the phase fronts 132a, 132b extend orthogonally relative to the direction of propagation of the optical beams, and angled (180–$\theta$) relative to each other. The length D of the excitation pattern formed by the overlapping optical pulses is related to the optical pulse duration $\tau$ and the crossing angle $\theta$ of the beams containing each pulse:

$$D = c\tau \sin^{-1}(\theta/2) \qquad (1)$$

where c is the speed of light in air ($3\times10^{10}$ cm/s). Equation 1 shows that D decreases linearly with the pulse width. As an example, a pair of optical pulses each having a duration of 30 fs crossed at an angle of 5° form an excitation pattern where d=200 microns. The number of light regions within the excitation pattern depends on the overlap of the "phase fronts" of the crossed optical beams. When the pulses 130a, 130b are crossed at time=$t_1$, optical interference occurs only in an area 140 that the phase fronts are overlapped; the angle between the fronts 132a', 132b' limits this area. The excitation pattern 152 formed by the optical interference consequently has a relatively small number of light regions. Specifically, the number of light regions generated using a pair of transform-limited pulses is about $2c\tau/\lambda$, where $\lambda$ is the optical wavelength. No more than about 20 fringes can be produced with pulses having a duration of 30 fs and a wavelength of 800 nm and $\lambda=10\mu$. Thus, generating a large number of light regions becomes increasingly difficult as the optical pulse duration decreases. This means that the intensity of the diffracted signal, and consequently the precision and accuracy of the corresponding film-thickness measurement, will generally decrease with the duration of the optical pulse.

FIG. 2A shows the case when the optical pulse is separated using a phase mask according to the invention. When imaged with a pair of confocal lenses, optical pulses 30a, 30b contain phase fronts 31a, 31b that are parallel to each other. In this case, the electric field (E) caused by the interfering optical beams in the image plane (z=0) of the optical system of FIG. 1 can be described as $$E = 2A_1 E_0 \cos(q_1 D/M) \exp(-t'^2/\tau_0^2) \exp(iw_o t') \qquad (2)$$

where $A_n$ is the complex amplitude depending on whether the grating is a phase or amplitude grating, q, is the wavevector equal to $2\pi/\lambda$, M is the magnification of the optical system, τ is the optical pulse duration, $E_o$ is a constant that depends on the amplitude of the optical pulse, and D is the spatial length of the pulse. The phase fronts 31a, 31b interfere in an area 141 that extends over the entire length of the fronts, thereby increasing the number of light regions in the excitation pattern. For an optical system containing a phase mask and an achromat lens pair performing 1:1 imaging, this number is limited by the number of periods of the phase mask pattern that are irradiated with the incident optical pulse. For example, a beam having a length of 200 microns that irradiates a pattern having a period of 10 microns (i.e., a wavelength of 5 microns) will generate an excitation pattern having about 40 fringes. The number of fringes is increased by either increasing the spot size of the optical pulses or decreasing the period of the phase mask pattern.

Figure 4A:
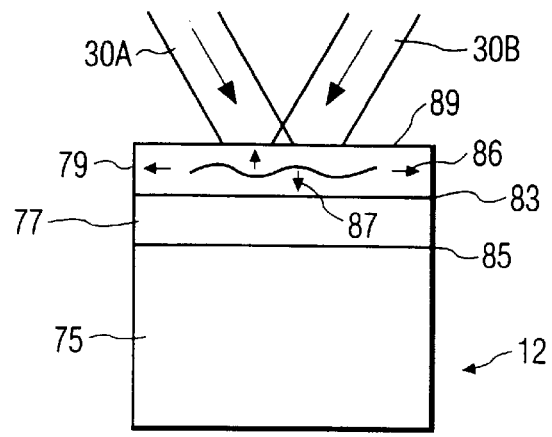
FIGS. 4A–4C are schematic side views of a multilayer structure showing, respectively, in-plane and out-of-plane acoustic waves being initiated with an excitation pattern; propagating through a first, exposed layer and a second, buried layer; and returning to a surface of the exposed layer.
Figure 4B:
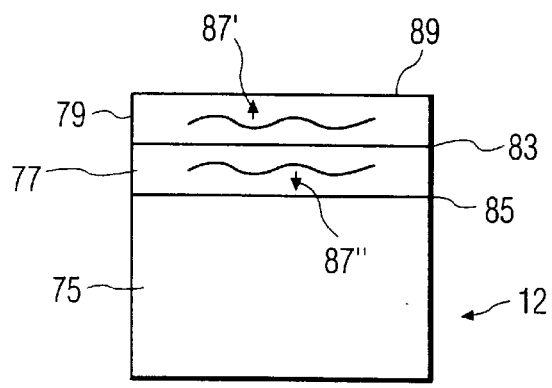
Figure 4C:
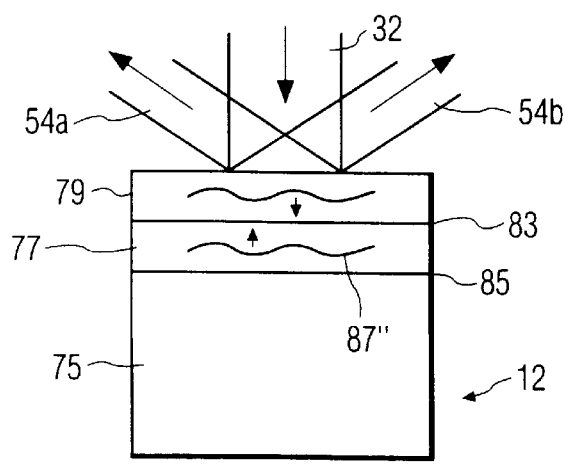

FIGS. 4A–4C shows how both in-plane and out-of-plane acoustic waves formed by the optical system shown in FIG. 1 can be generated, detected, and analyzed to simultaneously determine the thickness of each layer in a multilayer structure. Starting with FIG. 4A, a pair of short optical excitation pulses 30a, 30b are overlapped on a surface 89 of a multilayer structure 12 that includes a substrate 75, a buried layer 77, and an outer, exposed layer 79. The exposed 79 and buried 77 layers are separated by a first interface 83 (i.e., a "layer/layer interface"), and the buried layer 77 and substrate 75 are separated by a second interface 85 (i.e., a "layer/substrate interface"). As described above, the excitation pulses 30a, 30b overlap and interfere over their entire length D to form an excitation pattern that includes light and dark regions (not shown in the figure). Depending on the spot size, the phase mask in the optical system produces between 40 and 100 fringes in the excitation pattern when the pulse duration and wavelength are 100 fs and 800 nm, respectively.

As indicated in FIG. 4A, radiation is absorbed in the light regions of the excitation pattern to mildly heat the exposed layer 79, causing it to thermally expand. When the optical pulses are on the order of about 100 fs, this heating is "impulsive" and launches acoustic waves that have in-plane (indicated by arrow 86) and out-of-plane (indicated by arrow 87) components (for simplicity, only the out-of-plane components are shown in FIGS. 4B–4C). In FIG. 4B, the out-of-plane components 87 propagate toward the layer/layer interface 83. The spatial extent and amplitude of the acoustic pulses are determined by: 1) the optical pulse duration and spot size; 2) how strongly the excitation radiation is absorbed by the exposed layer; and 3) the thermal and electronic diffusion properties of the exposed layer. Once launched, the propagation characteristics of the out-of-plane components depend on: 1) the longitudinal sound velocity in the buried and exposed layers; 2) the acoustic impedance at each interface (i.e., the acoustic reflectivity); and 3) the acoustic dispersion of these layers. A more detailed description of these properties and the physics of acoustic wave excitation and propagation are described in, Shen et al., "Theory of Transient Reflecting Grating in Fluid/Metallic Thin Film/Substrate Systems for Thin Film Characterization and Electrochemical Investigation", Japanese Journal of Applied Physics, Vol. 35, pages 2339–2349 (1996), the contents of which are incorporated herein by reference.

FIG. 4B shows that the out-of-plane components 87 propagate through the exposed layer and impinge the layer/layer interface 83. There, reflected portions 87' of each of the components are sent back towards the surface 89 of the exposed layer; the reflection coefficient r at the interface is:

$$r = \frac{v_2\rho_2 - v_1\rho_1}{v_2\rho_2 + v_1\rho_1} \quad (3)$$

where $v_x$ and $\rho_x$ are, respectively, the longitudinal sound velocity and density of either the exposed (x=1) or buried (x=2) layer. Transmitted portions 87" of the out-of-plane components propagate through the layer/layer interface 83 and towards the layer/substrate interface 85. After impinging this interface, the components are reflected back through the layers and each interface as described above.

Referring to FIG. 4C, upon returning to the surface 89 of the exposed layer 79, the out-of-plane components cause either a small change to the optical reflection coefficient of the exposed layer or a surface ripple. These processes modulate the surface of the exposed layer in a spatially periodic pattern that matches the excitation pattern. As shown in FIG. 4C, the modulated surface diffracts a variably delayed optical probe pulse 32 to form a pair of signal beams 54a, 54b that are detected and analyzed as described below. By continually probing the surface at various times with a scanning mechanical delay stage, a round-trip time $\tau_{rt}$ of the acoustic pulses in each of the layers is determined.

FIGS. 5, 6A–6D and 7 indicate how data measured with the above-mentioned system is analyzed to determine the thickness of each layer in a multilayer system. In these cases, the samples were aluminum/titanium:tungsten/silicon structures, where aluminum and titanium:tungsten are thin (less than 3000 Å) layers. During a measurement process, data from the data-acquisition electronics is sent to a computer which generates a signal waveform 200 (step 300 in FIG. 8). The computer then compares the waveform 200 to a mathematical function (step 301 in FIG. 8) and iteratively adjusts parameters (e.g., film thickness) within the function (step 302 in FIG. 8). This process is repeated until a signal waveform 202 representing a "best fit" of the signal waveform 200 is generated (step 303 in FIG. 8). The best fit can be determined by minimizing a parameter that represents how accurately the simulated waveform compares to the signal waveform. For example, the parameter can be an $X^2$ or $R^2$ value generated by well-known fitting algorithms, such as the Marquant-Levenberg algorithm. The computer then determines the film thickness values used in the simulated waveform that give the best fit (step 304 in FIG. 8). These values are considered to be the actual thickness values of the measured structure.

The mathematical function that the computer uses to fit the signal waveform is based on the time and depth-dependent strain $\eta_{33}(z,t)$ induced by the acoustic waves that propagate out of the plane of the structure. The strain is defined as:

$$\eta_{33}(z,t) = \frac{(1-R)QB}{2\sigma c} \frac{1+v}{1+v}\left\{\exp\left(-\frac{z}{\sigma}\right) + \frac{1}{2}\exp\left[\frac{-|z-V_L t|}{\sigma}\right]\text{sign}(z-V_L t)\right\} \quad (4)$$

where R is reflectivity, Q is optical pulse fluence, B is the thermal expansion coefficient, L is the specific heat per unit volume, v is Poisson's ratio, $V_L$ is the longitudinal sound velocity in the film, σ is the distance that the optical pulses propagate into the exposed layer of the structure, t is time (i.e. the x axis of FIG. 5), and z represents the axis extending along the thickness of the layer. Equation (4) assumes that σ is significantly less than the distance separating light regions in the excitation pattern, and that z=0 at the exposed surface of the layer and increases positively into the layer. The first part of equation (4) represents static strain resulting from a density change due to a steady-state temperature rise induced by the excitation pattern. The second part of the equation describes the time-dependent strain induced by acoustic waves propagating out of the plane of the sample.

The computer compares the signal waveform to a simulated waveform that is described by:

$$f(t) = \left| iRk_2 h_o(t) + \frac{\delta R(t)}{2} \right|^2 \qquad (5)$$

where $k_2$ is a constant related to a Z component of the "wavevector" (defined as $2\pi/\Lambda$, where $\Lambda$ is the wavelength of the excitation pattern), $h_o(t)$ is a time-dependent function representing the surface ripple, and $\delta R(t)$ is a function representing time-dependent reflectivity changes in the sample.

The time-dependent surface ripple and reflectivity changes induced by the acoustic waves depend on the strain described in equation (4):

Surface Ripple $$h_o(t) = \int_0^\infty \eta_{33}(z, t) dz \qquad (6)$$

and Reflectivity $$\delta R(t) \alpha \int_0^\infty \exp\left[ i2K_z Z - \frac{2z}{\sigma} \right] \frac{K_{23} \eta_{33}(z, t) dz}{4\epsilon} \qquad (7)$$

where $K_{23}$ is the complex photoelastic constant of the layer and $\epsilon$ is the optical permitivity constant. The simulated waveform 202 shown in FIG. 5 indicates that surface ripple is the dominant process leading to diffraction of signal beams. Thus, to simplify the iterative fitting procedure, equations (5) and (6) can be used to analyze the signal waveform.

Figure 5:
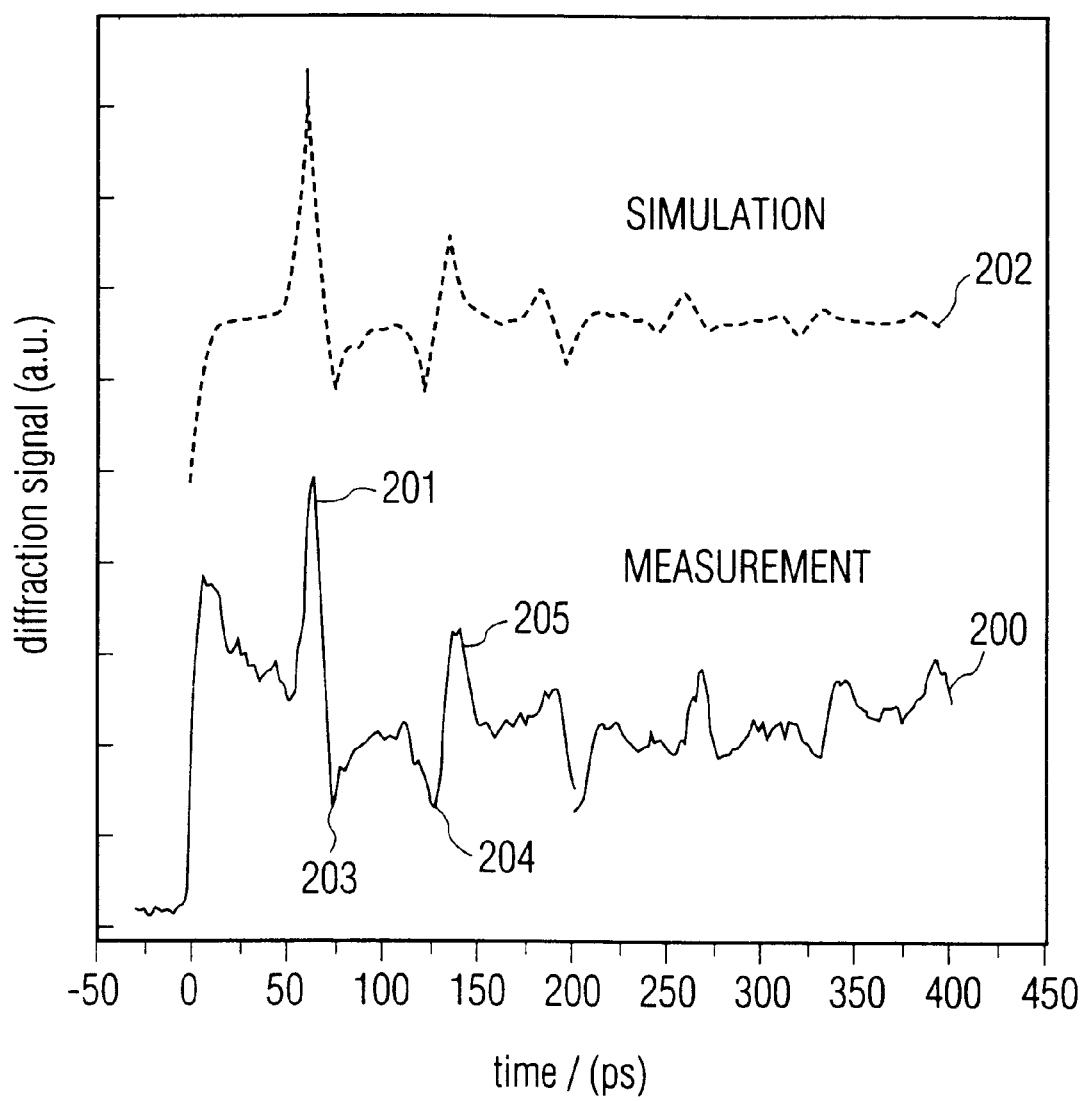
FIG. 5 is a graph of a time-dependent signal waveform measured with an optical apparatus similar to that shown in FIG. 1 from an aluminum titanium:tungsten/silicon structure and a simulated waveform generated using an aluminum thickness of 2000A and a titanium:tungsten thickness of 250A.

FIG. 5 shows a signal waveform 200 and the best-fit simulated waveform 202 generated by a computer using equations (4), (5) and (6) above. The signal waveforms for the figures were generated with an optical system similar to that shown in FIG. 1. To determine thickness values, the computer iteratively adjusted the thickness of the aluminum and titanium:tungsten layers until the simulated waveforms closely matched the signal waveforms.

FIGS. 5 and 6A–6D illustrate how the out-of-plane acoustic waves initiated with the optical system form peaks 201, 203, 204 and 205 in the signal waveform. The acoustic waves propagate in the aluminum/titanium:tungsten/silicon system, where aluminum is an outer layer 206, titanium:tungsten is a buried layer 207, and silicon is the substrate 208. The buried layer 207 and other layer 206 are separated by a layer/layer interface 209, and the buried layer 207 and substrate 208 are separated by a layer/substrate interface 210. The outer layer 206 has an exposed surface 211 that is measured as described above. The simulated waveform 202 used to fit the signal waveform 200 included an aluminum thickness of 2000 Å and a titanium:tungsten thickness of 250 Å.

Figure 6A:
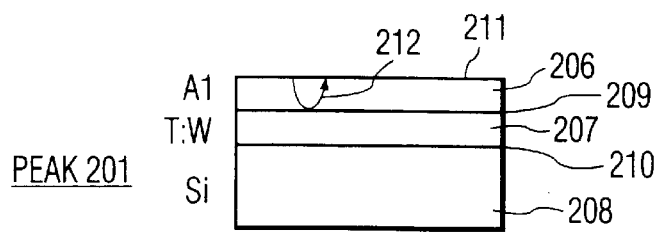
FIGS. 6A–6D show schematic side views of an out-of-plane acoustic wave propagating in a multilayer structure similar to that measured to generate the waveforms of FIG. 5.
Figure 6B:
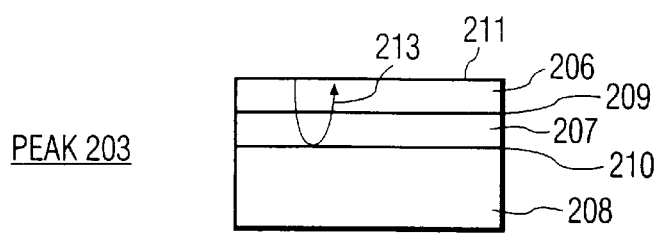
Figure 6C:
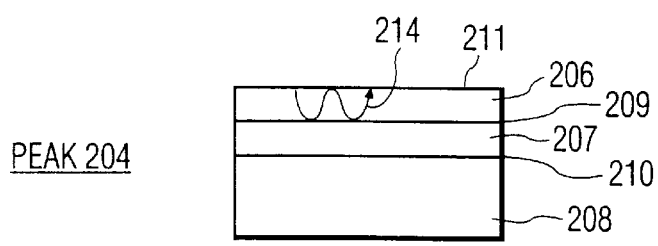
Figure 6D:
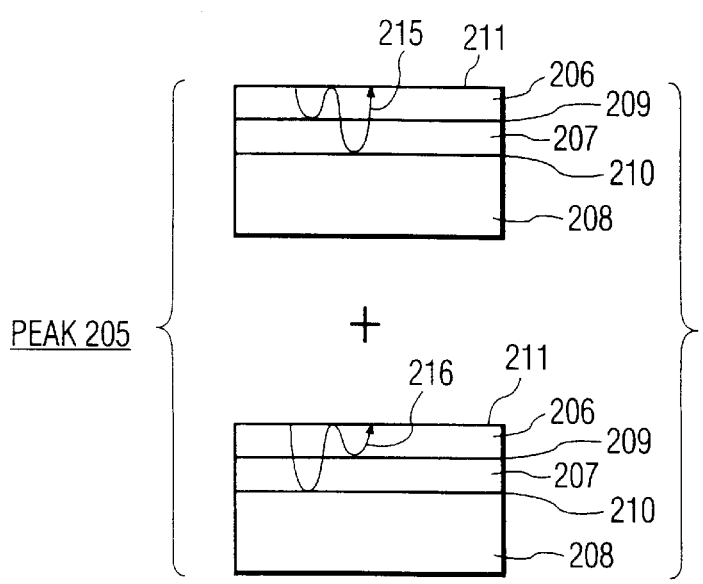

FIG. 6A shows how the peak 201 in the signal waveform 200 corresponds to an acoustic wave (indicated by the arrow 212) that propagates through the outer layer 206, reflects off the layer/layer interface 209, and returns to the surface 211 of the outer layer 206. In FIG. 6B, the second peak 203 in the signal waveform 200 corresponds to an acoustic wave (indicated by the arrow 213) that propagates through the outer 206 and buried 207 layers, reflects off the layer/substrate interface 210, and returns to the surface 211. In a similar fashion, FIG. 6C shows how an acoustic wave (indicated by the arrow 214) that makes two round trips in the outer layer generates peak 204 in the signal waveform 200. Similarly, FIGS. 6D and 6E show how two separate acoustic waves (indicated by the arrows 215 and 216) that propagate in both the outer 206 and buried 207 layers form peak 205 in the signal waveform.

Other Embodiments

Other embodiments are within the scope of the invention described above. In particular, optical systems other than that shown in FIG. 1 that use a phase mask to generate an excitation field can be used to initiate and detect acoustic waves. Such systems, for example, are described in U.S. Ser. No. 08/885,555 entitled IMPROVED TRANSIENT-GRATING METHOD AND APPARATUS FOR MEASURING MATERIAL PROPERTIES, the contents of which are incorporated herein by reference. In general, any optical system that includes both a phase mask and laser that generate optical pulses capable of initiating in-plane and out-of-plane acoustic waves can be used.

Likewise, the phase mask can be replaced with a similar diffractive optical element, such as an amplitude mask or an electro or acousto-optic modulator, to form the excitation pattern. The diffractive mask can include patterns that simultaneously generate more than one spatial frequency, an excitation pattern that is non-periodic, or an excitation pattern that contains light regions distributed in patterns other than a series of parallel lines. For example, the diffractive mask may generate an excitation pattern consisting of a series of concentric circles, ellipses, or other shapes. Other acceptable patterns are described in U.S. Pat. No. 5,734,470, entitled DEVICE AND METHOD FOR TIME-RESOLVED OPTICAL MEASUREMENTS, the contents of which have been previously incorporated herein by reference.

In other embodiments the optical system can be modified to increase the magnitude of the signal beam. For example, the signal magnitude can be increased using heterodyne amplification methods. In general, heterodyne amplification is done by spatially and temporally overlapping a phase component from an additional optical beam (called the heterodyne beam) with a phase component from the signal beam in a light-sensitive region of the photodetector. This process increases the amplitude of the signal measured at the detector, thereby enhancing the precision and accuracy of the thickness measurement.

Figure 7:
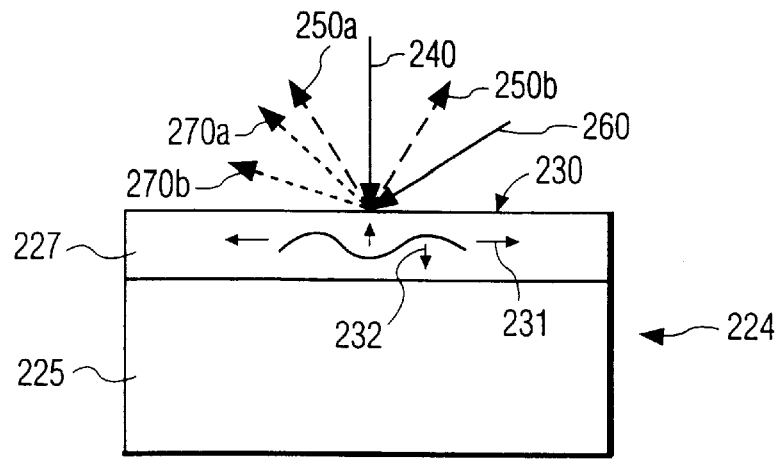
FIG. 7 is a schematic side view showing a film/substrate structure wherein both in-plane and out-of-plane acoustic waves are measured.
Figure 8:
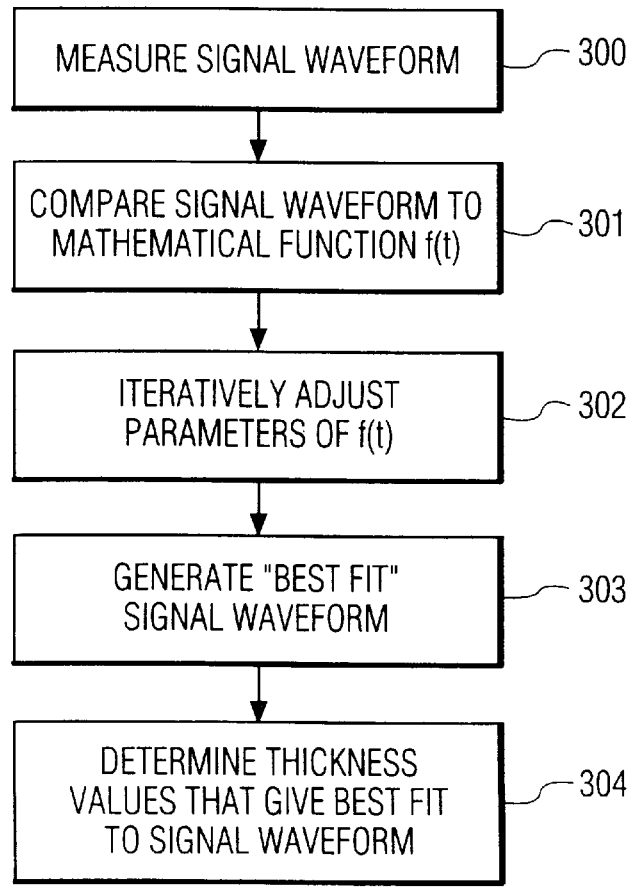
FIG. 8 is a flow chart showing a method for calculating the thickness of each layer in a multilayer structure according to the invention.

In another embodiment in-plane acoustic waves are simultaneously generated and detected along with the out-of-plane acoustic waves described above. The properties of the in-plane waves can then be analyzed to determine properties such as film thickness, delamination vs. adhesion, density, and other elastic, physical, and mechanical properties. FIG. 7 gives an example of this embodiment as applied to a simple, single-layer structure 224 containing a substrate 225 and a thin layer 227. In this case, both the in-plane (indicated by the arrow 231) and out-of-plane (indicated by the arrow 232) acoustic waves are excited with an excitation pattern as described above. Once excited, the out-of-plane acoustic waves are detected by irradiating a surface 230 of the structure 212 with a variably delayed probe pulse 240 similar to that shown in FIG. 1. Portions of the pulse are diffracted to form a pair of signal beams 250a,b which are detected as described above. These signal beams are then analyzed as a function of the probe pulse 240 delay to determine a properly (e.g., thickness) of the layer 227. The in-plane acoustic waves are simultaneously detected by irradiating the surface with a second probe beam 260 that has a relatively long duration (e.g., a pulse greater than 100 ns or a continuous-wave beam) compared to the width of the optical excitation pulses (typically less than 10 ps). Similar to the process described above, a portion of the probe beam 260 is diffracted by the in-plane acoustic waves to form a pair of signal beams 270a,b that are detected and analyzed to determine a property of the layer 227 (e.g., a sound velocity or thickness of the layer). In this way, data measured from both the in-plane and out-of-plane acoustic are used to enhance the accuracy of the measurement.

In still other embodiments the signal waveform generated by the optical system can be analyzed to determine other properties about the layers in the sample. For example, the shape of the echoes in the waveform can be analyzed to determine the degree of adhesion, surface roughness, or composition of one or more of the layers in the structure.

The light source can be any laser that generates optical pulses having a duration of less than about 10 ps or less and a wavelength that is strongly absorbed by the sample. For metal films, appropriate wavelengths are typically in the visible or near infrared spectral regions (e.g., 400 nm–800 nm). Lasers that produce these pulses are, for example, titanium:sapphire, chromium:LiSAF, ring, and fiber lasers.

The method and apparatus of the invention can be used to measure of variety of structures. For example, the method is particularly effective in determining the thickness of metal films used in the microelectronic industry. Such metal films include aluminum, copper, tungsten, titanium, tantalum, titanium:nitride, tantalum:nitride, gold, platinum, niobium, and alloys thereof. These metals may be included in single-layer and multilayer structures. Other materials that can be measured include polymers, diamond-like coatings, and buried transparent layers.

Still other embodiments are within the scope of the following claims.

What is claimed is:

1. An apparatus for measuring a property of a structure comprising at least one layer, comprising:
    a light source that produces an optical pulse having a duration of less than 10 ps;
    a diffractive element that receives the optical pulse and diffracts it to generate at least two excitation pulses;
    an optical system that spatially and temporally overlaps at least two excitation pulses on or in the structure to form an excitation pattern, containing at least two light regions, that launches an acoustic wave having an out-of-plane component that propagates through the layer, reflects off a lower boundary of the layer, and returns to a surface of the structure to modulate a property of the structure;
    a light source that produces a probe pulse that diffracts off the modulated property to generate at least one signal pulse;
    a detector that receives at least one signal pulse and in response generates a light-induced electrical signal; and
    an analyzer that analyzes the light-induced electrical signal to measure the property of the structure.

2. The apparatus of claim 1, wherein the diffractive element is a mask comprising an optically transparent substrate that includes a pattern made up of a series of grooves having a spatial periodicity of between 0.1 and 100 microns.

3. The apparatus of claim 2, wherein the diffractive mask is a phase mask that contains more than one pattern.

4. The apparatus of claim 1, wherein the diffractive element comprises a pattern that generates the two excitation pulses such that the two excitation pulses comprise phase fronts that are parallel when overlapped by the optical system.

5. The apparatus of claim 4, wherein the phase fronts of the overlapped optical pulses interfere to form a series of light regions that extend along an entire area of overlap of the optical pulses.

6. The apparatus of claim 1, wherein the optical system comprises at least one lens that collects and overlaps the excitation pulses on or in the structure.

7. The apparatus of claim 6, wherein the optical system comprises a lens pair having a magnification ratio of about 1:1.

8. The apparatus of claim 6, wherein the lens is positioned to receive the probe pulse and focus it onto the excitation pattern.

9. The apparatus of claim 8, wherein the lens is positioned to receive at least one signal beam and focus it onto the detector.

10. The apparatus of claim 6, wherein the optical system is an achromat lens pair.

11. The apparatus of claim 1, wherein the optical system comprises at least one mirror that reflects the excitation pulses onto the surface the structure.

12. The apparatus of claim 1, wherein the light source is a laser that generates an optical pulse having a duration of 2 ps or less.

13. The apparatus of claim 12, wherein the laser is a titanium:sapphire, chromium:LISAF, ring, or fiber laser.

14. The apparatus of claim 1, further comprising a mechanical delay line that delays the probe pulse relative to the excitation optical pulses.

15. The apparatus of claim 14, wherein the mechanical delay line comprises a galvanometer, rotating mirror, piezo-electric device, or an optical fiber.

16. The apparatus of claim 1, further comprising an optical heterodyne pulse configured to overlap with one of the signal beams on a light-sensitive region of the detector.

17. The apparatus of claim 1, wherein the analyzer is configured to analyze the light-induced electrical signal to determine a thickness of the layer.

18. The apparatus of claim 17, wherein the structure contains a plurality of layers, and the analyzer is configured to analyze the light-induced electrical signal to determine the thickness of each layer in the structure.

19. The apparatus of claim 18, wherein the analyzer is a computer that compares the light-induced electrical signal to a mathematical function.

20. The apparatus of claim 19 wherein the mathematical function models strain induced in the structure by the excitation pattern.

21. An apparatus for measuring a property of a structure comprising at least one layer, comprising:
    a first light source that produces an optical pulse having a duration of less than 10 ps;
    a diffractive element that receives the optical pulse and diffracts it to generate at least two excitation pulses;
    an optical system that collects and overlaps at least two excitation pulses on or in the structure to form an excitation pattern that launches: i) an acoustic wave comprising an out-of-plane component that propagates through the layer, reflects off a lower boundary of the layer, and returns to a surface of the structure; and ii) an acoustic wave comprising an in-plane component that propagates in the plane of the structure;
    a probe pulse from the first light source that diffracts off the surface of the sample to measure the out-of-plane component to generate a first signal pulse;
    a probe beam from a second light source that diffracts off the surface of the sample to measure the in-plane component to generate a second signal pulse;
    a first detector that receives the first signal pulse and in response generates a first light-induced electrical signal;
    a second detector that receives the second signal pulse and in response generates a second light-induced electrical signal;
    an analyzer that analyzes the first and second light-induced electrical signals to measure the property of the structure.

22. The apparatus of claim 21, wherein the diffractive element is a mask comprising an optically transparent substrate that includes a diffractive pattern made up of a series of grooves having a spatial periodicity of between 0.1 and 100 microns.

23. The apparatus of claim 22, wherein the diffractive mask is a phase mask that contains more than one diffractive pattern.

24. The apparatus of claim 21, wherein the diffractive element comprises a pattern that generates the two excitation pulses such that the two excitation pulses comprise phase fronts that are parallel when overlapped by the optical system.

25. The apparatus of claim 24, wherein the phase fronts of the overlapped optical pulses interfere to form a series of light regions that extend along an entire area of the overlap.

26. The apparatus of claim 21, wherein the optical system comprises at least one lens that collects and overlaps the excitation pulses on or in the structure with a magnification ratio of about 1:1.

27. The apparatus of claim 21, further comprising a mechanical delay line that delays the probe pulse relative to the excitation optical pulses.

28. The apparatus of claim 27, wherein the mechanical delay line comprises a galvanometer, rotating mirror, piezoelectric device, or an optical fiber.

29. The apparatus of claim 21, wherein the probe beam from the second light source comprises either a continuous-wave beam or a pulse that has a duration of greater than 100 nanoseconds.

30. The apparatus of claim 29, wherein the second light source is a diode laser.

31. The apparatus of claim 21, wherein the analyzer is configured to analyze the first light-induced electrical signal to determine the thickness of the layer.

32. The apparatus of claim 21, wherein the analyzer is configured to analyze the second light-induced electrical signal to determine at least one of: i) the thickness of the structure; ii) the thickness of a layer in the structure; iii) a density of a layer in the structure; and iv) a mechanical property of a layer in the structure.

33. The apparatus of claim 21, wherein the structure contains a plurality of layers, and the analyzer is configured to analyze the first and second light-induced electrical signals to determine the thickness of each layer in the structure.

34. A method for measuring a property from a structure comprising at least one layer, comprising the steps of:

passing an optical pulse having a duration of less than 10 ps through a diffractive element to generate at least two excitation pulses;

collecting and overlapping at least two excitation pulses on or in the layer to form an excitation pattern that contains at least two light regions;

launching an acoustic wave comprising an out-of-plane component that propagates through the layer, reflects off a lower boundary of the layer, and returns to a surface of the layer to modulate a property of the layer;

diffracting a probe pulse off the modulated property to generate at least one signal beam;

detecting the signal beam to generate a light-induced signal; and analyzing the light-induced signal beam to determine the property of the structure.

35. The method of claim 34, wherein the passing step further comprises passing the optical pulse through an optically transparent substrate that comprises a pattern comprising a series of grooves having a spatial periodicity of between 0.1 and 100 microns.

36. The method of claim 35, wherein the pattern diffracts the optical pulse to form two excitation pulses comprising phase fronts that are parallel when overlapped with the imaging system.

37. The method of claim 34, wherein the analyzing step further comprises analyzing the light-induced signal to determine the thickness of the layer in the structure.

38. A method for measuring a property from a structure comprising at least one layer, comprising the steps of:

passing an optical pulse having a duration of less than 10 ps from a first light source through a diffractive element to generate at least two excitation pulses;

collecting and overlapping at least two excitation pulses on or in the structure to form an excitation pattern that contains at least two light regions;

launching: i) an acoustic pulse comprising an out-of-plane component that propagates through the layer, reflects off a lower boundary of the layer, and returns to a surface of the structure; and ii) an acoustic wave comprising an in-plane component that propagates in the plane of the structure;

diffracting: i) a probe pulse from the first light source off the surface of the sample to measure the out-of-plane component to generate a first signal pulse; and ii) a probe beam from a second light source off the surface of the sample to measure the in-plane component to generate a second signal pulse;

detecting the first and second signal pulses to generate a first and second light-induced signal; and analyzing the first and second light-induced signals to determine the property of the structure.

* * * * *